US006783765B2

(12) United States Patent
Agrewala et al.

(10) Patent No.: US 6,783,765 B2
(45) Date of Patent: Aug. 31, 2004

(54) PROCESS FOR THE PREPARATION OF A VACCINE FOR THE TREATMENT OF TUBERCULOSIS AND OTHER INTRACELLULAR INFECTIONS DISEASES AND THE VACCINE PRODUCED BY THE PROCESS

(75) Inventors: Javed Naim Agrewala, Chandigarh (IN); Naresh Sharma, Chandigarh (IN)

(73) Assignee: Council of Scientific and Industrial Research, New Delhi (IN)

(*) Notice: Subject to any disclaimer, the term of this patent is extended or adjusted under 35 U.S.C. 154(b) by 0 days.

(21) Appl. No.: 09/815,602

(22) Filed: Mar. 23, 2001

(65) Prior Publication Data

US 2002/0136738 A1 Sep. 26, 2002

(51) Int. Cl.[7] .......................... A61K 39/04; A61K 39/02

(52) U.S. Cl. ....................... 424/248.1; 424/9.1; 424/9.2; 424/184.1; 424/201.1; 424/234.1; 424/237.1; 424/244.1; 424/258.1; 424/268.1; 424/269.1; 424/272.1

(58) Field of Search ........................ 424/9.1, 9.2, 184.1, 424/201.1, 234.1, 237.1, 244.1, 248, 258.1, 268.1, 269.1, 272.1, 248.1

(56) References Cited

PUBLICATIONS

Wiegeshaus et al "Evaluation of the protective potency of new tuberculosis vaccines", Reviews of Infectious Diseases, vol. 11, Supplement 2, Mar.–Apr. 1989, pp. S484–S490.*

* cited by examiner

*Primary Examiner*—Rodney P Swartz
(74) *Attorney, Agent, or Firm*—John W. Renner; Renner, Otto, Boisselle & Sklar

(57) ABSTRACT

The present invention relates to a process for the preparation of a vaccine against tuberculosis and other intracellular pathogens, this vaccine is targeted against intracellular pathogens, more particularly the pathogen *Mycobacterium tuberculosis* and Salmonella in this case.

4 Claims, 1 Drawing Sheet

Figure 1:
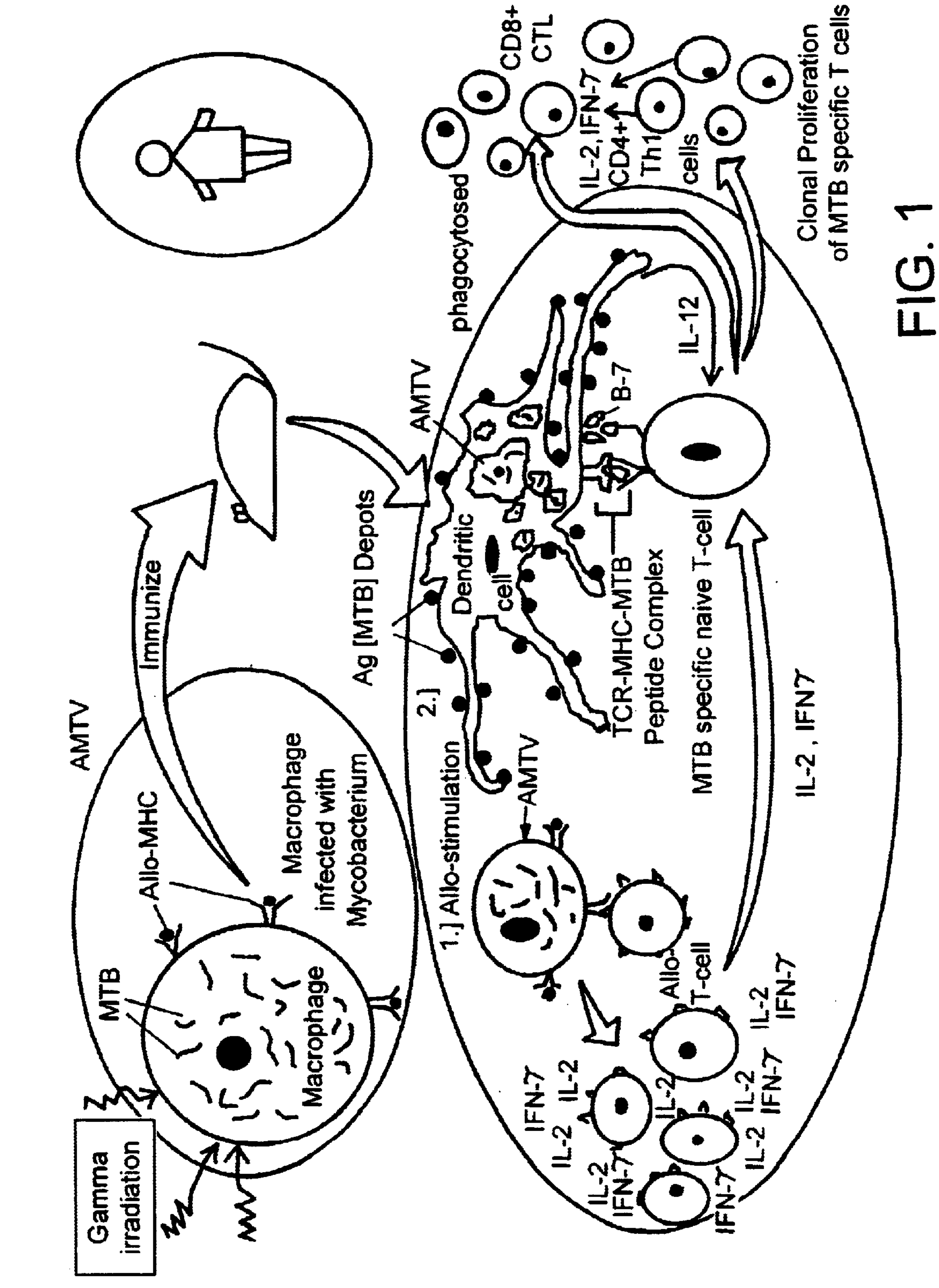

PROCESS FOR THE PREPARATION OF A VACCINE FOR THE TREATMENT OF TUBERCULOSIS AND OTHER INTRACELLULAR INFECTIONS DISEASES AND THE VACCINE PRODUCED BY THE PROCESS

FIELD OF INVENTION

The present invention relates to a process for the preparation of a vaccine against tuberculosis and other intracellular pathogens. This vaccine is targeted against intracellular pathogens, more particularly the pathogen *Mycobacterium tuberculosis* and Salmonella in this case.

The utility of the present invention is to develop a vaccine against the intracellular pathogens, which are causative agents of tuberculosis, brucellosis, leishmaniasis, listeriosis, leprosy, malaria, typhoid, trypanosomiasis and streptococcus and HIV-infection. The pathogen *Mycobacterium tuberculosis* (*M. tuberculosis*) the subject matter of this invention is a causative agent of tuberculosis. In this invention *M. tuberculosis* was allowed to grow in the allogeneic and syngeneic macrophages and macrophage cell lines. The macrophages—*M. tuberculosis* complex was then irradiated to kill the macrophages as well as the mycobacterium.

BACKGROUND OF THE INVENTION

Tuberculosis is a chronic infectious disease that continues to kill some 3 million people a year. About 8 million new cases arise every year and the number continues to increase. About one-third of the world population is infected with *M. tuberculosis*. The emergence of AIDS has reactivated tuberculosis in millions of dormant individuals, causing a sharp rise in the number of cases and deaths. *M. tuberculosis* is therefore responsible for the highest morbidity rate among all infectious agents. The only available vaccine BCG is both unpredictable and highly variable. Doubtful efficacy of BCG vaccination has put the scientific community to urgently develop effective means of vaccination against the *M. tuberculosis* (Bloom, B. R. et. al., Annu. Rev. Immunol. 10:1992:453).

During the past many decades BCG has been extensively used as a vaccine world over. Several hundred million children and new born have been the recipient of BCG vaccine. However, in spite of wide usage of BCG vaccine, tuberculosis has still become the fastest spreading disease not only in developing countries but also in the industrialized world. Further, the protective efficacy of the current BCG vaccine is both unpredictable and highly variable and it remains the most controversial of all currently used vaccines. Its doubtful efficacy in controlled trials have increased the concern about its use as a vaccine (Bloom and Fine, Tuberculosis In B. Bloom (ed.), 1994:531, Bloom, B. R. et. al., Annu. Rev. Immunol. 10:1992:453). Furthermore, the extensive clinical trials done in Madras showed similar extent of protection in BCG-vaccinated and unvaccinated individuals, indicating that BCG induced zero protection (*Ind. J. Med. Res.* 1980:72(Suppl.):1–74). Thus it is obvious that BCG vaccination does not prevent transmission.

In past also, many questions always arose pertaining to the safe use of BCG vaccine.

A major catastrophe that cast a cloud over the reputation of BCG vaccination occurred in 1929. In Lubeck, Germany, 251 children received a BCG vaccine prepared at a local institute, and 72 of these children died. Subsequent investigation revealed that the institute also maintained cultures of virulent tubercle bacilli and that the batch of BCG vaccine given to the children had accidentally been contaminated with one of these strains of *Mycobacterium tuberculosis* (Lubeck. 1935. *Die Sauglingstuberkulose in Lubeck*. Springer, Berlin).

A new question has arisen regarding the safety of BCG in HIV-infected individuals. A small number of cases of disseminated BCG-osis have been reported among children who received BCG vaccine and were subsequently found to be HIV seropositive (Von Reyn, et. al. *Lancet* 1987: ii:669–672; Braun, et. al., *Pedietr. Infect. Dis. J.* 1992:11:220–227; Weltman, et. al., *AIDS* 7:1993:149). WHO currently recommends discontinuing the use of BCG vaccine in children showing overt signs of immunodeficiency (World Health Organization, 1992, *Expanded Program for Immunization, Program Report*,World Health Organization, Geneva; *Weekly Epidemiol. Rec.* 62:1987:53).

Large volunteer studies by Dahlstrom and Difts (Scand J Respir Dis Suppl. 65:1968:35) and a meta-analysis of BCG in the prevention of tuberculosis based on 13 prospective studies and 10 case control studies has recently been completed (Colditz et. al., J. Amer. Med. Assoc. 271:1994:698–702). While it concluded that on average BCG was about 50% protective in preventing tuberculosis, the biological and operational significance of averaging, in essence, such widely divergent results are itself arguable.

Before the advent of AIDS, in most wealthy countries, the incidence of tuberculosis was declining for at least a century. This is illustrated in comparisons between The Netherlands (which never employed BCG vaccination) and the United Kingdom and Scandinavia (which instituted national BCG vaccination in the 1950). The declines in tuberculosis cases reported in these countries were similar (Styblo, K., Selected Papers R. Netherland Tuberc. Assoc. 24:1991:136; Sutherland, Bull. Int. Union. 57:1981:17). Thus it is unreasonable to attribute that the decline was due to BCG vaccination alone.

BCG's performance is based on a hypothesis that BCG is effective against primary infection in children and endogenous reactivation of long-standing infections but not against exogenous infection (ten Dam, H. G. *Adv. Tuberc. Res.* 21:1984:79; ten Dam, H. G. and A. Pio. *Tubercle* 63:1988:226). Epidemiological data suggest that BCG vaccination imparts greater or more consistent protection against systemic disease, in particular miliary tuberculosis and tuberculosis meningitis in children, than against pulmonary disease (Rodrigues, et.al., Int J epidemiol. 22:1993:1154). Lurie's studies indicated that the number of CFU of *M. tuberculosis* isolated from lungs of BCG-immunized versus unimmunized rabbits showed no difference in the number of organisms reaching and capable of being cultured from lung and other tissues.

Another insight is provided by the intracellular location of the mycobacterium. Electron microscopic findings indicate that BCG remains essentially entirely within the phagolysosomes after in vitro infection of macrophages, whereas virulent *M. tuberculosis* (strain H37Rv) can escape from the phagolysosome and enter the cytoplasm (McDonough, et.al., *Infect. Immun.* 61:1993:2763). This may be relevant insofar as it is the antigens in the endosomal compartment of antigen-presenting cells that are presented in conjunction with MHC class II determinants to $CD4^+$ T helper cells, whereas cytoplasmic antigens are presented in association with the Major Histocompatibility Complex (MHC) class I determinants to $CD8^+$ Cytotoxic T cells (CTL). If these findings in vitro are general, they will explain why *M.*

*tuberculosis* is more dependent for its elimination on MHC class I-restricted CTL than BCG and suggests that BCG may not be very effective in eliciting MHC class I-restricted CTL (Stover, et.al., Nature 351:1991:456). In this context, Rich, 1951 (The Pathogenesis of Tuberculosis, $2^{nd}$, p. 1028; Charles C Thomas, Publisher, Springfield, Ill.), Canetti, 1955 (The Tubercule Bacilli in the Pulmonary Lesion of Man, p. 226; Springer, N.Y.) and Lurie, 1964 (Resistance to Tuberculosis. Experimental Studies in Native and Acquired Defense, p. 391; Harvard University Press, Cambridge Press, Cambridge, Mass.), commented that recovery from infection with *M. tuberculosis* provided stronger protection against future tuberculosis than could BCG.

The effective resistance to *M. tuberculosis* infection will require participation both of specific $CD8^+$ CTL to lyse macrophages or parenchymal cells unable to restrict their infection and of specific $CD4^+$ T cells able to produce IL-2, IFN-γ, TNF-α, and other lymphokines involved in macrophage activation.

Considering these drawbacks of the BCG-vaccine, the applicants have taken advantage of the fact that the vaccine will be used as an irradiated preparation and has no fear of inoculating in AIDS patients and immunocompromised children. BCG is given as an attenuated preparation and is not recommended in these subjects because it causes disseminated BCG-osis, WHO currently recommends discontinuing the use of BCG vaccine in children showing overt signs of immunodeficiency (World Health Organization. 1992. *Expanded Program for Immunization. Program Report*. World Health Organization, Geneva. World Health Organization. *Weekly Epidemiol. Rec.* 1987:62:53–54).

Another insight is provided by the intracellular location of the mycobacterium. BCG remains essentially entirely within the phagolysosome of macrophages, whereas virulent *M. tuberculosis* can escape from the phagolysosome and enter the cytoplasm (McDonough, K. A., Y. Kress, and B. R. Bloom. 1993. *Infect Immun.* 61:2763–2773). The antigens in the endosomal compartment of antigen-presenting cells are presented in conjunction with MHC class II determinants to $CD4^+$ T helper cells, whereas cytoplasmic antigens are presented in association with the Major Histocompatibility Complex (MHC) class 1 determinants to $CD8^+$ Cytotoxic T cells. *M. tuberculosis* is more dependent for its elimination on MHC class I-restricted CTL. BCG is not effective in eliciting MHC class I-restricted CTL (Stover, et.al., Nature 351:1991:456). The present vaccine contains the irradiated preparation of *M. tuberculosis* grown in macrophages. *M. tuberculosis* infected macrophages are reported to effectively generate CTL (Stover, et.al., Nature 351:1991:456). Further, it has also been reported that irradiated cells undergo apoptosis and can be phagocytosed by the dendritic cells (Albert, M. L., et.al., Nature 392:1998:86) and it leads to the generation of antigen specific $CD4^+$ and $CD8^+$ T cell response. This apoptosis-dependent pathway may not only have potential in vaccination studies but also for therapeutically manipulating immune system to induce T-helper and CTL response in vivo to a variety of antigens including tumor, and possibly to modulate favourable immune response.

Rich (The pathogenesis of Tuberculosis. $2^{nd}$ ed, p. 1028, 1951. Charles C Thomas, Publisher, Springfield, Ill.), Canetti (The tubercle Bacillus in the pulmonary Lesion of Man, p. 226, 1955. Springer, N.Y.), and Lurie (Resistance to Tuberculosis. Experimental Studies in Native and Acquired Defense, 391, 1964. Harvard University Press, Cambridge, Mass.) have commented that recovery from infection with *M. tuberculosis* provided stronger protection against future tuberculosis than could BCG. In context with the above statements, the candidate vaccine has advantage over existing BCG vaccine because it contains the *M. tuberculosis* grown in the natural environment of the macrophages that secrete the unique antigens responsible for the induction of protective immune response and can generate $CD4^+$ T-helper cells and $CD8^+$ CTL. The effective resistance to *M. tuberculosis* infection will require participation of both specific $CD8^+$ CTL to lyse macrophages or parenchymal cells unable to restrict their infection and of specific $CD4^+$ T cells able to produce IL-2, IFN-γ, TNF-α, and other lymphokines involved in macrophage activation.

The main rationale behind this process was to develop a vaccine against tuberculosis and other intracellular diseases, MHC-matched (syngeneic) and mismatched (allogeneic) macrophages harboring *M. tuberculosis* on irradiation undergo apoptosis; dendritic cells engulf these macrophages and present the antigen (Mycobacterium-proteins and allo-macrophage peptides) on their surface and induce naïve T-cells to differentiate into effecter CD4* Th1 cells. These dendritic cells also activate CD8* T cells for cell-mediated immunity. Allo-macrophages in the system generate an allo-reaction and as a result a large amount of cytokines like IL-2, IL-12, IFN-γ, etc., are produced which promote the Th1 response and cell mediated immune response. It is known that Th1-type of response provides protection against tuberculosis. Hence the main utility of the process was to produce a potent and specific vaccine against *M. tuberculosis.*

OBJECTS OF THE INVENTION

The main object of the present invention thus is to develop a vaccine against tuberculosis and other intracellular diseases like leprosy, leishmaniasis, typhoid, trypanosomiasis malaria, brucellosis, listeriosis, AIDS, streptococcal infection and cancer.

Another object of the present invention is to culture the pathogen inside the syngeneic and allogeneic macrophages and allow them to secrete antigens within the cells.

Yet another object is to develop a method whereby the pathogen are killed by the already known drugs and further will be gamma irradiated before use; the gamma irradiated cells are known to undergo apoptosis and are engulfed by the dendritic cells. Dendritic cells are potent activator of Th1 cells and CD8+ cytotoxic cells.

Another object is to develop a vaccine that acts against both syngeneic macrophages entrapped pathogens (viz. *M. tuberculosis, M. leprae*, leishmania, salmonella, trypanosoma, malaria, brucella, listeria, HIV, streptococcus) (e.g. SMTV, S=syngeneic, M=macrophage, T=tuberculosis, V=vaccine) and allogeneic-macrophages entrapped pathogen vaccine (e.g., AMTV, A=allo, M=macrophage, T=tuberculosis, V=vaccine), to generate protective immune response.

Still another objective of the present invention is to develop a vaccine based on entrapment of pathogen in the allogeneic cells that would elicit immune response irrespective of the genetic background i.e. it will work as a promiscuous vaccine, and hence it will work irrespective of the genetic diversity in the human subjects.

SUMMARY OF THE INVENTION

The present invention relates to a process for the preparation of a vaccine against tuberculosis and other intracellular pathogens. This vaccine is targeted against intracellular pathogens, more particularly the pathogen *Mycobacterium tuberculosis* and Salmonella in this case.

DESCRIPTION OF THE ACCOMPANYING DRAWINGS

FIG. 1 represents schematically the process of how Allo-Macrophage Tuberculosis (AMTV) works.

DETAILED DESCRIPTION OF THE INVENTION

The novelty in the present invention is that the protective antigens secreted by the mycobacterium inside the macrophages can be used as a vaccine without isolating them from the macrophages.

The vaccine was used after irradiation and the irradiated cells are known to undergo apoptosis. The cells undergoing apoptosis were engulfed by the dendritic cells. Dendritic cells activated naïve T cells to differentiate into Th1 cells and cytotoxic cells. These cells are known to be cardinal in imparting protective immunity against intracellular infections and cancer.

Allo-macrophages in the system generated allo-reaction as a result large amount of cytokines like IL-2, IL-12, IFN-γ, etc., are produced which promote the Th1 response and cell mediated immune response. The allogeneic cells used in the construction of vaccine would elicit immune response irrespective of the genetic background i.e. it will work as a promiscuous vaccine. Hence it can used in human subjects irrespective of the genetic diversity.

The aim of the present invention is to develop a vaccine against tuberculosis, salmonella and other intracellular infections. *M. tuberculosis* and *Salmonella typhimurium* was cultivated in allogeneic (AMTV) and syngeneic (SMTV) macrophages and was killed by γ-irradiation and was used as a vaccine. The AMTV in vivo will preferably be engulfed by dendritic cells (γ-irradiation causes cells to undergo apoptosis and dendritic cells engulf apoptotic cells) and will then activate the mycobacterium reactive naïve T cells. Allogeneic macrophages being used for immunization worked as an adjuvant and elicited allogeneic reactive T cells that produced huge amount of IL-2, IFN-γ, IL-12. These cytokines are vital for the growth and differentiation of naïve T cells to $CD4^+$ and $CD8^+$ effector T cells. Dendritic cells are the preferred Antigen Presenting Cells (APC) for Th1 and cytotoxic T cells (CTL). Th1 and $CD8^+$ CTL are principal cells in generating effective and protective immunity against *M. tuberculosis*. The tuberculosis resistant and susceptible strains of mice were inoculated with the vaccine.

FIG. 1 represents schematically the process of how Allo-Macrophage Tuberculosis (AMTV) works.

The rationale behind the process of how Allo-Macrophage Tuberculosis (AMTV) works has been schematically shown in FIG. 1. *M. tuberculosis* was cultivated in MHC-mismatched (allogeneic) and syngeneic macrophages. This preparation was γ-irradiated and used as vaccine. The AMTV in vivo will preferably be engulfed by dendritic cells (as it is known that γ-irradiation causes cells to undergo apoptosis and dendritic cells engulf apoptotic cells) and will then activate the mycobacterium reactive naïve T cells. However, macrophages loaded with mycobacterium cannot activate naïve T cells directly. Allogeneic macrophages being used for immunization would elicit allogeneic reactive T cells that produce huge amount of IL-2, IFN-γ, IL-12. These cytokines are vital for the growth and differentiation of naïve T cells to $CD4^+$ and $CD8^+$ effector T cells. Dendritic cells are the preferred Antigen Presenting Cells (APC) for Th1 and cytotoxic T cells (CTL). They cause stimulation of naïve T cells to differentiate into antigen reactive Th1 cells and cytotoxic T lymphocytes. Moreover, dendritic cells trap foreign antigen (in this case mycobacterium antigen) and act as a reservoir, slowly releasing the antigen in the system for the activation of T cells and for the maintenance of memory cells. IL-2, IFN-γ and IL-12 secreted by alloreactive T cells will engineer the clonal expansion of mycobacterium reactive Th1 and cytotoxic T cells. Th1 and $CD8^+$ CTL are cardinal in generating effective and protective immunity against *M. tuberculosis*. The tuberculosis resistant and susceptible strains of mice were inoculated with the vaccine.

The rationale behind the process of how Allo-Macrophage Tuberculosis (AMTV) works has been demonstrated by cultivating *M. tuberculosis* cultivating in MHC-mismatched (allogeneic) and syngeneic macrophages. This preparation was γ-irradiated and used as vaccine. The AMTV in vivo will preferably be engulfed by dendritic cells (as it is known that γ-irradiation causes cells to undergo apoptosis and dendritic cells engulf apoptotic cells) and will then activate the mycobacterium reactive naïve T cells. However, macrophages loaded with mycobacterium cannot activate naïve T cells directly. Allo-macrophages being used for immunization will elicit allo-reactive T cells that produce huge amount of IL-2, IFN-γ, IL-12. These cytokines are vital for the growth and differentiation of naïve T cells to $CD4^+$ and $CD8^+$ effector T cells. Dendritic cells are the preferred Antigen Presenting Cells (APC) for Th1 and cytotoxic T cells (CTL). They cause stimulation of naïve T cells to differentiate into antigen reactive Th1 cells and cytotoxic T lymphocytes. Moreover, dendritic cells trap foreign antigen (in this case mycobacterium antigen) and act as a reservoir, slowly releasing the antigen in the system for the activation of T cells and for the maintenance of memory cells. IL-2, IFN-γ and IL-12 secreted by alloreactive T cells will engineer the clonal expansion of mycobacterium reactive Th1 and cytotoxic T cells. Th1 and CTL are cardinal in generating effective and protective immunity against *M. tuberculosis* (Albert, M. L., et. al., Nature 392:1998:86; Wang, B. et. al., Proc. Natl. Acad. Sci. USA 90:1993:4156) The tuberculosis resistant and susceptible strains of mice were vaccinated with AMTV and SMTV. The efficacy of the vaccine was monitored by infecting the mice with live *M. tuberculosis* and monitoring their mortality and viable counts of the bacteria in the lungs, spleen and liver The vaccinated (4–12 weeks) mice were challenged with $10^5$–$10^6$ viable *M. tuberculosis* H37Rv. The lungs, spleens and livers of the infected mice were removed after an additional period of 3–4 weeks and serial dilutions of organ homogenate was plated on agar plates to establish the number of viable tubercle bacilli residing in these organs. The vaccinated animals were also monitored for the generation of Th1 and Th2 cells by measuring IFN-γ and IL-4. The vaccine was inoculated in the mouse footpad and the induction of delayed type hypersensitivity reaction was monitored by measuring the thickness of the footpad.

According to the present invention there is provided a novel vaccine against tuberculosis and other intracellular pathogens and a process for the development thereof. The tuberculosis vaccine (SMTV and AMTV), comprise *M. tuberculosis* cultivated in MHC-matched and mismatched-macrophages. The preparations are irradiated and used as distinct vaccines.

Since the vaccine fulfill all the requirements necessary for generating favourable immune response against *M.*

*tuberculosis*, it has been anticipated that such preparations should work effectively against tuberculosis.

The vaccine AMTV works in a promiscuous manner, since it does not follow the rules of MHC-restriction and is based on allo-stimulation and engulfment of foreign-apoptotic cells by dendritic cells. Whereas the vaccine SMTV works in MHC-restriction fashion.

The infected cells were grown in sufficient quantity and stored after isoniazid treatment and γ-irradiation. The preparation was thoroughly checked for viable mycobacterium by viability counting. None of the bacteria were viable in the vaccine. The mice were vaccinated intraperitoneally or subcutaneously with vaccine and were challenged with viable *M. tuberculosis* H37Rv. The viability of the tubercle bacilli residing in lungs, spleens and livers was monitored. The animals were immunized with the vaccine and the uptake of the apoptotic cells by dendritic cells was documented by immunofluorescence. The animals were vaccinated with SMTV and AMTV and the proliferation and differentiation of naïve $CD4^+$ Th cells into effector Th1 and Th2 subtype was studied. As a control, *M. tuberculosis* entrapped in syngeneic macrophages was also used. The ability of SMTV and AMTV to generate $CD8^+$ cytotoxic T cells was monitored by the standard $Cr^{51}$-release assay.

To test the hypothesis of allo-stimulation, Balb/c ($IA^d$) and C57BL/6 ($IA^b$) strains of mice were immunized with ovalbumin entrapped in mitomycin C treated allogeneic and syngeneic APC. To eliminate the possibility of preferably generating allo-response in secondary response, the haplotype of the allo-APC was changed. The animals were given secondary booster with ovalbumin entrapped in the APC of CBA ($IA^k$) mice. Profound activation of $CD4^+$ and $CD8^+$ T cells was observed. Antigen-specific-T cell proliferation and predominant Th1 response were noticed, as evidenced by mainly the production of IL-2 and IFN-γ and IgG2a-isotype. High production of IL-2 in allo-response was noticed which indicates that the immunization with the antigen entrapped in allo-APC treated with mitomycin C undergoes apoptosis. The apoptotic cells are engulfed by dendritic cells that then evokes mycobacterium specific and the allo-reactive T cells response. The allo-T cells are >10% of the total T cell population and are known to induce high secretion of IL-2. IL-2 produced by allo-T cells then engineers the proliferation of antigen specific T cell.

Therefore, in the present invention the development of effective tuberculosis vaccine; based on a novel delivery system targeted to dendritic cells, *M. tuberculosis* was cultivated in the macrophage cell line viz. J77.4 or allogeneic and syngeneic macrophages. The infected macrophages were isoniazid treated and irradiated and then used for vaccination studies in protection against *M. tuberculosis.*

The rationale behind the process of how Allo-Macrophage Tuberculosis (AMTV) works has been demonstrated by cultivating *M. tuberculosis* cultivating in MHC-mismatched (allogeneic) and syngeneic macrophages. This preparation was γ-irradiated and used as vaccine. The AMTV in vivo will preferably be engulfed by dendritic cells (as it is known that γ-irradiation causes cells to undergo apoptosis and dendritic cells engulf apoptotic cells) and will then activate the mycobacterium reactive naïve T cells. However, macrophages loaded with mycobacterium cannot activate naïve T cells directly. Allo-macrophages being used for immunization will elicit allo-reactive T cells that produce huge amount of IL-2, IFN-γ, IL-12. These cytokines are vital for the growth and differentiation of naïve T cells to $CD4^+$ and $CD8^+$ effector T cells. Dendritic cells are the preferred Antigen Presenting Cells (APC) for Th1 and cytotoxic T cells (CTL). They cause stimulation of naïve T cells to differentiate into antigen reactive Th1 cells and cytotoxic T lymphocytes. Moreover, dendritic cells trap foreign antigen (in this case mycobacterium antigen) and act as a reservoir, slowly releasing the antigen in the system for the activation of T cells and for the maintenance of memory cells. IL-2, IFN-γ and IL-12 secreted by alloreactive T cells will engineer the clonal expansion of mycobacterium reactive Th1 and cytotoxic T cells. Th1 and CTL are cardinal in generating effective and protective immunity against *M. tuberculosis* (Albert, M. L., et. al., Nature 392:1998:86; Wang, B. et. al., Proc. Natl. Acad. Sci. USA 90:1993:4156). The tuberculosis resistant and susceptible strains of mice were vaccinated with AMTV and SMTV. The efficacy of the vaccine was monitored by infecting the mice with live *M. tuberculosis* and monitoring their mortality and viable counts of the bacteria in the lungs, spleen and liver. The vaccinated (4–12 weeks) mice were challenged with $10^5$–$10^6$ viable *M. tuberculosis* H37Rv. The lungs, spleens and livers of the infected mice were removed after an additional period of 3–4 weeks and serial dilutions of organ homogenate was plated on agar plates to establish the number of viable tubercle bacilli residing in these organs. The vaccinated animals were also monitored for the generation of Th1 and Th2 cells by measuring IFN-γ and IL-4. The vaccine was inoculated in the mouse footpad and the induction of delayed type hypersensitivity reaction was monitored by measuring the thickness of the footpad.

Accordingly, the present invention provides a vaccine against tuberculosis and other intracellular pathogens selected from the group consisting of *Mycobacterium leprae*, leishmania, salmonella, typanosoma, plesmodium, brucella, listeria, HIV, streptococcus and cancer. The invention also provides a method for the development of the said vaccine, comprising the steps of:

(i) culturing pathogens selected from the group comprising *Mycobactenum tuberculosis, Mycobactenum leprae*, leishmania, salmonella, typanosoma, plasmodium, brucella, listeria, HIV, and streptococcus;

(ii) culturing syngeneic (same strain), allogeneic (different strain) and xenogeneic (different species like sheep and goat) macrophages and macrophage cell lines selected from the group consisting of J774, P388D1, RAW, BMC-2, THP-1, etc.;

(iii) infecting macrophages and cell lines with a pathogen;

(iv) treating the infected cells with known drugs followed by gamma irradiation to obtain the vaccine;

(v) immunizing disease resistant and susceptible strains of animals with the vaccine obtained above;

(vi) infecting the animals with live pathogen and monitoring their mortality and viable counts of infectious agent in lungs, spleen and liver; and (vii) monitoring the vaccinated animals for proliferation and generation of CD4* Th1 and Th2 cells and CD8* cytotoxic T cells indicating the generation of cell mediated immunity.

The invention further provides a process for the preparation of a vaccine against tuberculosis, wherein the said process comprising the steps of:

(i) culturing of *Mycobacterium tuberculosis* H37Rv;

(ii) culturing of syngeneic and allogeneic macrophages and macrophage cell lines selected from the group consisting of J774, P388D1, RAW, BMC-2, THP-1, etc.;

(iii) infecting macrophages and cell lines (J774, P388D1, RAW, BMC-2, THP-1) with *M. tuberculosis;*

(iv) treating the infected cells with isoniazid and gamma irradiation to obtain the vaccine;

(v) immunizing tuberculosis resistant and susceptible strains of mice with allogeneic macrophagetuberculosis vaccine (AMTV) and syngeneic macrophage tuberculosis vaccine (SMTV) obtained above;

(vi) infecting the mice with live *M. tuberculosis* and monitoring their mortality and viable counts of bacteria in lungs, spleen and liver;

(vii) monitoring the vaccinated animals for proliferation and generation of CD4* Th1 and Th2 cells and CD8* cytotoxic T cells indicating the generation of cell mediated immunity; and (viii) inoculating the vaccine in the mouse footpad and examining the delayed type hypersensitivity reaction by measuring the swelling in the footpad for protective immunity.

The invention also provides a process for the preparation of a vaccine against salmonella, wherein the said process comprising the steps of:

(i) culturing of *Salmonella typhimurium;*

(ii) culturing of syngeneic and allogeneic macrophages and macrophage cell lines selected from the group consisting of J774, P388D1, RAW, BMC-2, THP-1, etc.;

(iii) infecting macrophages and cell lines (J774, P388D1, RAW, BMC-2, THP-1) with *S. typhimurium;*

(iv) treating the infected cells with mitomycin C and gamma irradiation to obtain the vaccine;

(v) immunizing tuberculosis resistant and susceptible strains of mice with the vaccine obtained above;

(vi) infecting the mice with live *S. typhimurium* and monitoring their mortality and viable counts of bacteria in lungs, spleen and liver;

(vii) monitoring the vaccinated animals for proliferation and generation of CD4* Th1 and Th2 cells and CD8* cytotoxic T cells indicating the generation of cell mediated immunity; and (viii) inoculating the vaccine in the mouse footpad and examining the delayed type hypersensitivity reaction by measuring the swelling in the footpad for protective immunity.

The invention provides a vaccine by entrapment of *M. tuberculosis*, Salmonella and other intracellular pathogens in the allogeneic and syngeneic macrophages and using it for the protection against the infectious agent.

The process of the present invention is illustrated in the examples given below which should not, however, be constructed to limit the scope of the present invention.

EXAMPLE 1

A Process for the Preparation of a Vaccine Against Tuberculosis and Other Intracellular Pathogens The intracellular pathogens viz. *Mycobacterium tuberculosis, Mycobacterium leprae*, leishmania, salmonella, trypanosoma, plasmodium, brucella, listeria, HIV, streptococcus were cultured in the macrophages of syngeneic and allogeneic mice, macrophages cell lines J774, P338D1, RAW, BMC-2, THP-1 (ATCC, Rockville). The infected cells were treated with isoniazid (20 $\mu$g/ml) for 48h at 37° C./5% $CO_2$ and irradiated at 0.05 kGy.

(i).

(a) The resultant infected cells were treated with the pathogen specific drug and further irradiated and was used as a vaccine and their efficacy was monitored by challenging the vaccinated mice with the viable bacteria. The efficacy of the vaccine was monitored by counting the viability of the infectious organism in the lungs, spleens and livers of the infected mice by serial dilutions of organ homogenate plated on the agar plates after definite interval of time. Similarly, the unvaccinated animals were challenged with live bacteria and were monitored for their mortality and viable counts in lungs, spleens and livers.

(b) The vaccinated animals were monitored for proliferation and differentiation of $CD4^+$ Th cell into bacteria reactive effector cytotoxic T cells, Th1 and Th2 cells by measuring IFN-γ and IL-4 by ELISA.

(c) $CD8^+$ cytotoxic T cells were monitored by $^{51}Cr$-release assay.

EXAMPLE 2

A Process for the Preparation of a Vaccine Against Tuberculosis

In another example, *Mycobacterium tuberculosis* H37Rv obtained from Central JALMA Institute for Leprosy, Agra, was cultured in the macrophages of syngeneic and allogeneic mice, macrophages cell lines J774, P338D1, RAW, BMC-2, THP-1 (ATCC, Rockville). The infected cells were treated with isoniazid (20 $\mu$g/ml) for 48 h at 37° C./5% $CO_2$ and irradiated at 0.05 kGy.

(i).

(a) The resultant infected cells were treated with isoniazid and then gamma irradiated to use as a vaccine and their efficacy was monitored by challenging the vaccinated mice with $10^5$–$10^6$ viable bacteria. In this case the lungs, spleens and livers of the infected mice were removed after an additional period of 3–4 weeks and serial dilutions of organ homogenate was plated on agar plates to establish the number of viable *M. tuberculosis* residing in the these organs. Similarly, the unvaccinated animals were challenged with live bacteria and were monitored for their mortality and viable counts in lungs, spleens and livers.

(b) The vaccinated animals were monitored for proliferation and differentiation of T cells into bacteria reactive effector $CD8^+$ cytotoxic T cells and $CD4^+$ Th1 and Th2 cells by measuring IFN-γ and IL-4 by ELISA.

(c) $CD8^+$ cytotoxic T cells were monitored by $^{51}Cr$-release assay.

(d) The vaccine was inoculated in the mouse footpad and the delayed type hypersensitivity reaction was monitored by measuring the thickness of the footpad.

EXAMPLE 3

A Process for the Preparation of a Vaccine Against Salmonella

In another example, *Salmonella typhimurium* (MTCC98) was cultured in the macrophages obtained from syngeneic and allogeneic mice and macrophages cell lines J774, BMC-2 and RAW. The infected cells were treated with mitomycin C (50 $\mu$g/ml) and gamma irradiated (0.05 kGy).

(i).

(a) The resultant infected cells were treated with the drug and irradiated and were used as a vaccine and their efficacy was monitored by challenging the vaccinated mice with $10^5$–$10^6$ viable bacteria. The animals were observed for mortality for 21 days. The lungs, spleens and livers of the infected mice were removed and serial dilutions of organ homogenates was plated on agar plates to establish the number of viable salmonella bacilli residing in these organs. Similarly, the unvaccinated animals were challenged with live bacteria and were monitored for their mortality and viable counts in lungs, spleens and livers.

(b) The vaccinated animals were monitored for proliferation and differentiation of $CD4^+$ Th cell into bacteria reactive effector Th1 and Th2 cells by measuring IFN-γ and IL-4 by ELISA.

(c) $CD8^+$ cytotoxic T cells were monitored by $^{51}Cr$-release assay.

(d) The vaccine was inoculated in the mouse footpad and the delayed type hypersensitivity reaction was monitored by measuring the thickness of the footpad.

ADVANTAGES

The main advantages of the present invention are:

(i) About one-third of the world population is infected with *M. tuberculosis*. About 5–10% only develop active tuberculosis and the 90% of the individual develop effective immunity against the *M. tuberculosis. M. tuberculosis* present in the host macrophages secretes unique antigens, which are the effective inducers of long lasting protective immunity. In contrast, *M. tuberculosis* when cultured in vitro in artificial medium, secrete antigens that do not induce optimum level of protection and the immunity generated is short lived. The outstanding feature in the process is that the protective antigens of mycobacterium secreted inside the macrophages were utilized without isolating them from the macrophages.

(ii) These allo-macrophages used in the system functions as a unique system for delivering antigens secreted by live mycobacterium to dendritic cells and as an adjuvant for eliciting the secretion of cytokines viz. IL-2, IL-12, IFN-γ, etc., from allo-reactive T cells. The excess of IL-2 secreted was utilized by the mycobacterium reactive protective T cells. Therefore there was no need for any adjuvant to be used. Alloreactive T cells produce chiefly IL-2, IFN-γ and IL-12, the cytokines responsible for the generation of Th1-like immune response. Th1 are crucial for inducing protective immunity against *M. tuberculosis.*

(iii) The advantage of the invention is that the γ-irradiated mycobacterium infected macrophages were engulfed by dendritic cells. The γ-irradiated cells are known to undergo apoptosis. Apoptotic cells taken up by the dendritic cells induce the activation of $CD4^+$ Th1 and $CD8^+$ cytotoxic T cells. Cytotoxic T cells are responsible for the killing of macrophages infected with mycobacterium. Lysis of target is essential in the case of diseases like tuberculosis, typhoid, leprosy, leishmaniasis, AIDS, etc., where the pathogen reside and multiplies within the macrophages. Lysis of these cells liberates the pathogen and gives an opportunity to activated macrophages to engulf the bacteria and eliminate it. Dendritic cells express high level of B7-1 and secrete IL-12 and are only potent APC that can activate naïve T cells. Moreover, dendritic cells can differentiate naïve T cells to Th1 and $CD8^+$ cytotoxic T cells. Th1 and cytotoxic T cells are vital for induction of protective immunity against *M. tuberculosis* (Wakeham, et. al., J. Immunol., 160:1998:6101).

(iv) Another advantage and uniqueness in the invention is that the dendrites on dendritic cells trap the foreign antigens and work as a reservoir. This antigen is slowly released from the dendrites, and is responsible for the maintenance of memory cells.

(v) The AMTV vaccine works in MHC-unrestricted manner, because it is based on allo-stimulation and engulfment of apoptotic cells by dendritic cells. It will work for all human, irrespective of the genetic diversity.

What is claimed is:

1. A process for the preparation of a vaccine against an intracellular pathogen selected from the group consisting of *M. tuberculosis, M. leprae*, Leishmania, Salmonella, Trypanosoma, Plasmodium, Brucella, Listeria, and Streptococcus, wherein the process comprises the steps of:

(i) culturing the intracellular pathogen;

(ii) culturing syngeneic (same strain), allogeneic (different strain) and xenogeneic (different species like sheep and goat) macrophages and macrophage cell lines selected from the group consisting of J774, P388D1, RAW, BMC-2 and THP-1;

(iii) infecting the macrophages and macrophage cell lines with the selected pathogen of step (i);

(iv) treating the infected macrophages and macrophage cell lines with pathogen specific drugs to kill the pathogen, followed by gamma irradiation to kill the macrophage or macrophage cell line and remaining pathogens to obtain a composition;

(v) immunizing disease resistant and susceptible strains of animals with the composition;

(vi) infecting the vaccinated animals with live selected pathogen and monitoring animal mortality, and viable counts of the pathogen in lungs, spleen and liver;

(vii) monitoring the vaccinated animals for proliferation and generation of CD4* Th1 and Th2 cells and CD8* cytotoxic T cells indicating the generation of call mediated immunity against the pathogen; and (viii) wherein the composition is a vaccine if administration of the composition results in decreased mortality of vaccinated animals and/or decreased viable counts of the pathogen in lungs, spleen, and liver of the infected animals when compared to non-immunized animals.

2. A process for the preparation of a vaccine against tuberculosis, the process comprising the steps of:

(i) culturing *M. tuberculosis* H37Rv;

(ii) culturing syngeneic, allogeneic and xenogenic macrophages and macrophage cell lines selected from the group consisting of J774, P388D1, RAW, BMC-2 and THP-1;

(iii) infecting the macrophages and macrophage cell lines (J774, P388D1, RAW, BMC-2, THP-1) with *M. tuberculosis;*

(iv) treating the infected macrophage and macrophage cell lines with amikacin, isoniazid and gamma irradiation to kill the macrophage or macrophage cell line and remaining *M. tuberculosis* to obtain a composition;

(v) immunizing tuberculosis resistant and susceptible strains of mice with an allogeneic macrophage tuberculosis composition or syngeneic macrophage tuberculosis composition or xenogenic macrophages tuberculosis;

(vi) infecting the vaccinated group of mice with live *M. tuberculosis* and monitoring animal mortality, and viable counts of *M. tuberculosis* in lungs, spleen and liver;

(vii) monitoring the vaccinated animals for proliferation and generation of CD4* Th1 and Th2 cells, and CD8* cytotoxic T cells indicating the generation of cell mediated immunity against *M. tuberculosis*; and (viii) wherein the composition is a vaccine if administration of the composition results in decreased mortality of vaccinated animals and/or decreased viable counts of *M. tuberculosis* in lungs, spleen, and liver of the infected animals when compared to non-immunized animals.

3. A process for the preparation of a vaccine against salmonella, the process comprising the steps of:

(i) culturing *Salmonella typhimurium;*

(ii) culturing syngeneic, allogeneic macrophages and xenogenlc macrophages and macrophage cell lines selected from the group consisting of J774, P388D1, RAW, BMC-2 and THP-1;

(iii) infecting the macrophages and macrophage cell lines (J774, P388D1, RAW, RMC-2, THP-1) with *S. typhimurium;*

(iv) treating the macrophage and macrophage cell lines with mitomycin C and gamma irradiation to kill the macrophage or macrophage cell line and remaining *S. typhimurium* to obtain a composition;

(v) immunizing salmonella resistant and susceptible strains of mice with the composition;

(vi) infecting the vaccinated group of mice with live *S. typhimurium* and monitoring animal mortality, and viable counts of *S. typhimurium* in lungs, spleen and liver, (vii) monitoring the vaccinated animals for proliferation and generation of CD4* Th1 and Th2 cells, and CD8* cytotoxic T cells indicating the generation of cell mediated immunity against *S. typhimurium*; and (viii) wherein the composition is a vaccine if administration of the composition results in decreased mortality of vaccinated animals and/or decreased viable counts of *S. typhimurium* in lungs, spleen, and liver of the infected animals when compared to non-immunized animals.

4. A vaccine as prepared by the process as claimed in claim 1, wherein by entrapment of *M. tuberculosis, Salmonella typhimurium* and other intracellular pathogens in the allogeneic, syngeneic and xenogenic macrophages, the preparations being treated by the available drugs selected from amikacin, isoniazid and gamma radiation for tuberculosis and mitomycin C and gamma radiation for *S. typhimurium* to kill the pathogens and the vaccine is further gamma irradiated before being used for the protection against the infectious diseases.

* * * * *